Figure 6:
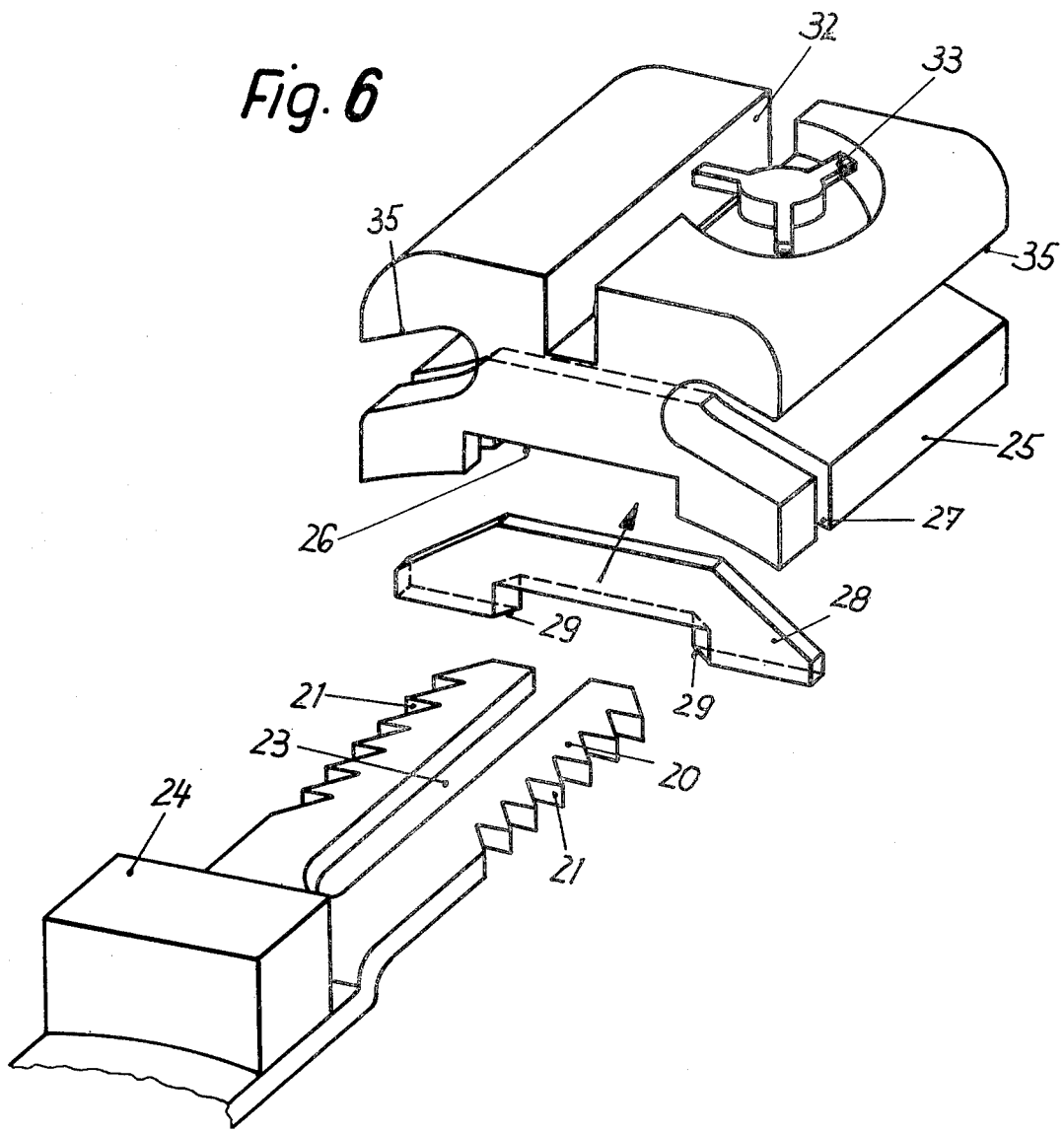

United States Patent [19]

Förster

[11] 4,167,813
[45] Sep. 18, 1979

[54] DENTAL FIXING ELEMENT

[75] Inventor: Rolf Förster, Pforzheim, Fed. Rep. of Germany

[73] Assignee: Bernhard Förster, Pforzheim, Fed. Rep. of Germany

[21] Appl. No.: 792,193

[22] Filed: Apr. 29, 1977

[30] Foreign Application Priority Data

May 20, 1976 [DE] Fed. Rep. of Germany ....... 2622467
Jan. 17, 1977 [DE] Fed. Rep. of Germany ....... 2701715

[51] Int. Cl.² .............................................. A61C 7/00
[52] U.S. Cl. ................................................. 32/14 A
[58] Field of Search ...................................... 32/14 A

[56] References Cited

U.S. PATENT DOCUMENTS

| | | | |
|---|---|---|---|
| 1,304,881 | 5/1919 | Johnson | 32/14 A |
| 2,007,517 | 7/1935 | Boyd et al. | 32/14 A |
| 2,011,575 | 8/1935 | Ford | 32/14 A |
| 2,104,192 | 1/1938 | Ford | 32/14 A |
| 3,138,872 | 6/1964 | Lazarus | 32/14 A |
| 3,740,849 | 6/1973 | Rubin | 32/14 A |
| 3,922,787 | 12/1975 | Fisher et al. | 32/14 A |

Primary Examiner—Russell R. Kinsey
Assistant Examiner—John J. Wilson

[57] ABSTRACT

The element is adapted to be fitted as an annular band around a tooth and to be secured to a dental appliance to hold the same in position. The fixing element comprises a strip metal element having two end portions, which are adapted to overlap in said annular band, two slide-snap fastener parts which are respectively carried by said end portions and selectively interengageable in a plurality of positions which determine respective diameters of said annular band, and one of the fastener parts including a bracket which is provided with a longitudinal groove for slidably receiving an orthodontic appliance. The bracket carries a clamping device which projects over the longitudinal groove, and is selectively and angularly movable to positions for slidable and clamping engagement with the orthodontic appliance received in the longitudinal groove.

10 Claims, 9 Drawing Figures

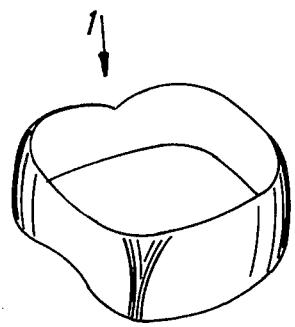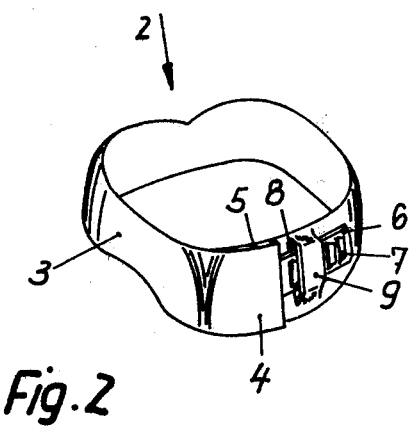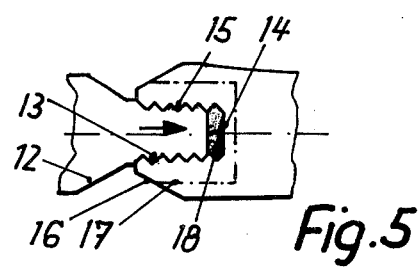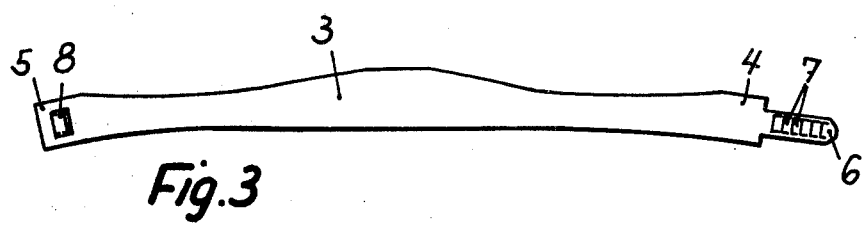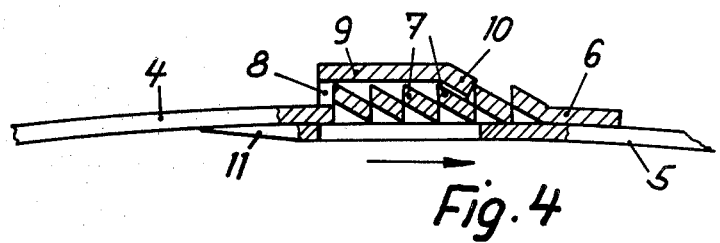

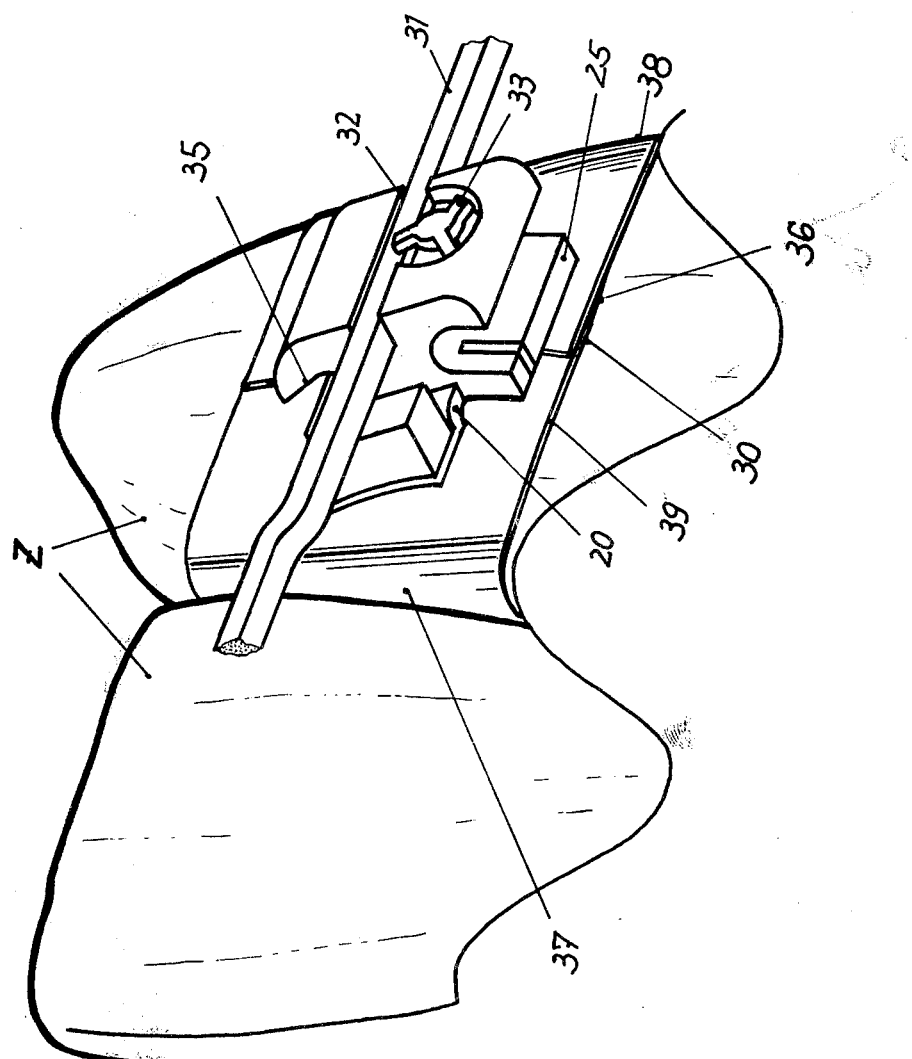

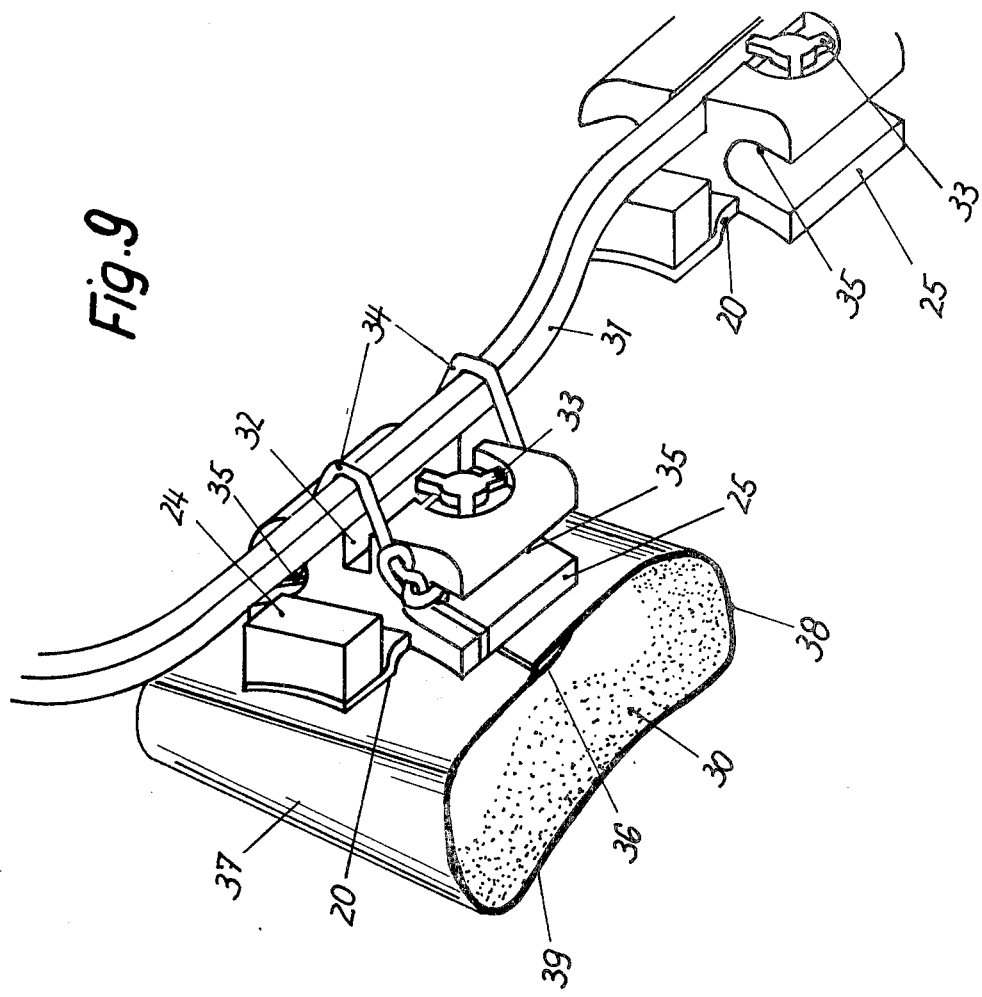
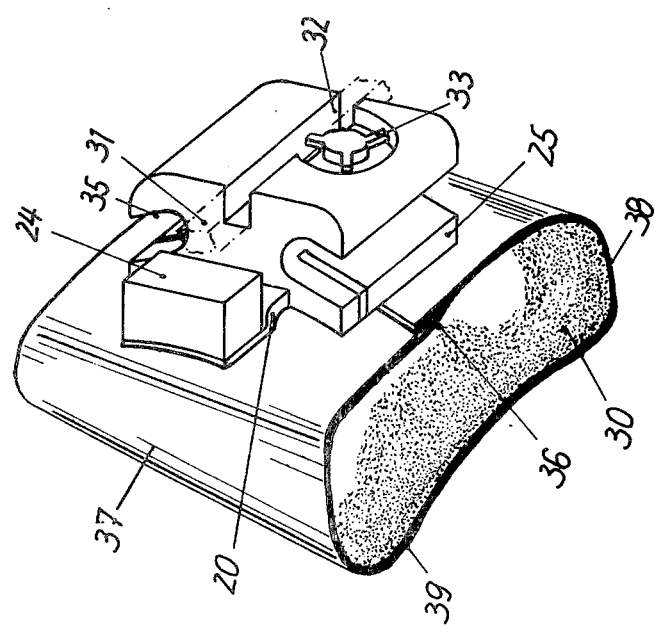

DENTAL FIXING ELEMENT

This invention relates to a strip metal element for dental purposes, specifically for use as a fixing and supporting element, which is intended to be fitted around a tooth and to be connected to an orthodontic or prosthetic appliance to hold it in position.

It is known to use pre-shaped strip metal elements for dental purposes, specifically for use as a fixing and supporting element, which is intended to be fitted around a tooth and connected to an orthodontic or prosthetic appliance to hold it in position. These elements are usually made in that a piece of metal strip is formed to an annular band, which is slidably fitted over the tooth for fixation. Even if a very large number of such annular bands in different shapes are available for teeth which differ in size and shape, a satisfactory fit cannot be ensured so that clearance spaces between the tooth and the annular band must be filled with cement. In the course of time, this cement filling is washed out and remains of food deposit in this region and initiate caries. To adapt the annular band to the anatomic shape of the tooth, the dentist must turn inwardly the outer edge of the annular band. This requires a high dexterity and takes much time, just as the remaining work of adaptation.

It is an object of the invention to facilitate the adaptation of the preformed strip metal element to the tooth, to reduce the number of such pre-shaped strip metal elements which must be kept in stock, and to optimize the fixation of the strip metal elements to the tooth. In a strip metal element for orthodontic purposes, specifically for use as a fixing and supporting element, which is intended to be applied around a tooth and connected to an orthodontic or prosthetic appliance to hold it in position, this object is accomplished in that the end portions of the strip metal element have preferably beveled surfaces and are adapted to overlap and provided with slide-snap fastener parts which permit of an adjustment of the strip metal element to fit around the tooth. The fastener parts at the ends of the strip metal element can first be interengaged in a preliminary position, in which the element can easily be slipped over the tooth, and the fastener can then be tightened so that the thin-walled, pliable strip metal element conforms to the shape of the tooth. When the strip metal element is tightened by means of suitable forceps, the strip metal element will automatically hug the tooth so that no clearance space is left.

Specifically, the outer end portion of the strip may consist of a tongue which is formed with struck-out, inclined toothlike lugs, which are slidably movable through an eyelet formed in the other end portion of the strip metal element to a position which determines the diameter of the resulting annular band.

In another embodiment of the slide-snap fastener providing for an adjustment of the strip metal element, one end portion of the strip metal element is provided with a serrated plug-in tongue and the other end portion is provided with a keeper having a receiving passage and locking shoulders so that the manipulation and fitting also on the buccal side of the tooth are facilitated.

Another object of the invention is to save space in that the slide-clamp fastener constitutes also a bracket for an adjustable connection of orthodontic arches.

A further object of the invention is to provide an improved bracket adapted to be secured to an orthodontic or prosthetic appliance in a selected position.

In the adjustable strip metal element comprising end portions that are adapted to overlap and provided with slide-snap fastener parts, the overlapping end portions may have beveled surfaces and the strip metal element may have thinner portions adapted to contact the tooth on its mesial and distal sides. This feature eliminates the need for separating the teeth from each other at the lateral points of contact. The strip metal element may be shaped so that it flares toward its proximal edge when the fastener has been closed so that the tightening of the element causes the same to adapt itself snugly to the root of the tooth and no cement is required in this region.

Further details of illustrative embodiments of the pre-shaped strip metal element provided with a slide-snap fastener will now be described more fully with reference to the drawings, in which FIG. 1 is a perspective view of a known preshaped annular band which has been formed from strip metal, FIG. 2 is a perspective view showing an annular band made from a strip metal element according to the invention, FIG. 3 is a developed view showing the annular band of FIG. 2, FIG. 4 is an enlarged sectional view showing a slide-snap fastener, FIG. 5 is an enlarged top plan view showing another slide-snap fastener, FIG. 6 is an exploded view of a plug-in tongue and a keeper having a receiving passage, FIG. 7 is a perspective view showing the fastener of FIG. 6 when the strip metal element has been closed in annular shape and applied around an incisor and combined with an orthodontic arch, FIG. 8 is a perspective view showing the assembly of FIG. 7 without the incisor, for greater clarity, and FIG. 9 is a perspective view showing the assembly of FIG. 8 in conjunction with additional means for fixing the orthodontic arch.

As is apparent from FIG. 1, the known pre-shaped strip metal elements for fixing orthodontic or prosthetic appliances to teeth consist of annular bands 1, which are slidably fitted over a tooth to which the appliance is to be fixed. For this purpose, such annular bands must be available in a very large number of shapes and sizes. Nevertheless, a close fit of the annular bands is not ensured so that clearance spaces are liable to remain and must be filled with cement, which promotes caries.

The annular band 2 according to the invention, shown in FIG. 2, has been made from a strip metal element 3, which is shown in FIG. 3 and has overlapping end portions 4, 5 which comprise parts of a slide-snap fastener, as is shown in FIG. 4. The outer end portion 4 of the strip metal element terminates in a tongue 6, which is formed with struck-out inclined toothlike lugs 7 and can be inserted into an eyelet passage 8 formed in the second end portion 5 to a position which determines the diameter of the resulting annular band for a close adaptation to the shape and size of the tooth. This adaptation will be promoted by the use of a suitable forceps for tightening the band.

Particularly from the enlarged view shown in FIG. 4 it is apparent that the struck-out inclined toothlike lugs 7 constitute resilient barbs which when the tongue 6 is inserted into the eyelet passage 8 lock the tongue against being pulled back. It is apparent that the bridgelike portion 9 defining the eyelet passage has a resilient angled portion 10, which is adapted to interfit with each of the toothlike lugs. The end portion 5 terminates in a tip 11, which is beveled on the inside toward its extremity so that a formation of a clearance space in this region is avoided.

FIG. 5 is an enlarged view showing another embodiment of a slide-snap fastener. One end portion 12 of the strip metal element is formed with side teeth 13, which are insertable into a covered recess 14, which is formed in the second strip end portion 16 and provided with mating teeth 15. The end portion 12 is insertable into the opening 14 to a position which determines the diameter of the resulting annular band. The recess 14 is covered by a strip portion 17. In the position shown in FIG. 5, a space 18 is left for further adjustment. It is apparent that the side teeth 13 constitute barbs, which during the insertion into the recess 14 interlock with the teeth 15 thereof to prevent a pulling back of the end portion 12.

From the exploded view of FIG. 6, a plug-in tongue 20 is apparent, which is provided with side teeth 21 and with a central slot 23, which permits of a resilient interengagement of the teeth as the tongue 20 is inserted, also a handle 24 for inserting the tongue 20, and a keeper 25 which is formed with a passage 26 for receiving the tongue 20 and with a transverse slot 27 for receiving a locking member 28, which is formed with mating teeth 29, which present locking shoulders that have seeking edges and are adapted to interengage with the teeth 21 of the tongue 20 as the same is inserted.

In the embodiment shown in FIGS. 7 to 9, the plug-in tongue 20 and the keeper part 25 are mounted on the ends of the strip metal element 30 and are interengaged to close said element in the form of an annular band. The band is applied to an incisor in such a manner that the slide-snap fastener is disposed on the buccal side of the tooth, as is shown in FIG. 7 for teeth Z.

In the embodiment shown in FIGS. 7 and 8 the keeper 25 constitutes also a bracket, which slidably receives the arch 31 in a longitudinal groove 32 and is provided with a rotatable clamping member 33, which has radial arms for clamping the arch 31 in the groove 32. The clamping arms of the clamping member 33 differ in thickness. FIG. 7 shows the annular band 30 fitted around a tooth Z.

FIG. 9 shows another keeper 25, which also constitutes a bracket, to which the orthodontic arch 31 is connected by loops 34 of a tying element, which extends in side grooves 35 of the bracket. Such an arrangement is required when the incisors are set back to such an extent that the orthodontic arch used to straighten the teeth cannot be clamped in the manner shown in FIGS. 7 and 8. Just as in FIG. 7, the annular band is fitted around a tooth. A second bracket is indicated, which may be fixed, e.g., to the next tooth.

It is also apparent from FIGS. 7 to 9 that the tip of the inner end portion of the band has a beveled inside surface 36 tapering to the extremity and that the annular bands 30 have thinner portions 37 and 38 for contacting the teeth on their mesial and distal sides. As a result, it is not necessary to insert rubber wedges or wires between the teeth to separate them before the annular band 30 can be fitted and there is no need to apply cement to the annular band at the extremity of its inner end portion. Such cement was previously required and when it had been washed out the tooth was liable to be attacked by remains of food retained in this region. The annular band 30 may flare toward its proximal edge 39 so that the tightening of the annular band 30 causes the same to fit closely around the root of the tooth and leaves also in this region no clearance space which would have to be filled with cement. Such cement was required in the previous practice and was liable to be washed out so that the tooth was then attacked by remains of food retained in this region and caries was thus prmoted.

To improve the grip on the orthodontic arch, two brackets according to the invention may be mounted one beside the other on a strip metal element. In that case, only one of these brackets may be used as a keeper part of the slide-snap fastener whereas both brackets serve to hold the orthodontic arch in position. In another embodiment, two brackets may be arranged one over the other and may serve as keeper parts of the slide-snap fastener and, if desired, to hold orthodontic arches in position.

What is claimed is:

1. A bracket which is adapted to be secured to an orthodontic appliance and has a longitudinal groove for slidably receiving an orthodontic appliance and carries a clamping device which comprises a plurality of radial clamping arms which differ in thickness and are angularly spaced apart, and projects over said groove and is selectively angularly movable to positions for slidable and clamping engagement, respectively, with an orthodontic appliance received in said groove so that said clamping device is adapted to secure the bracket to said orthodontic appliance in a selected position.

2. A dental fixing element which is adapted to be fitted as an annular band around a tooth and to be secured to a dental appliance to hold the same in position, comprising a strip metal element having two end portions, which are adapted to overlap in said annular band, and two slide-snap fastener parts which are respectively carried by said end portions and selectively interengageable in a plurality of positions which determine respective diameters of said annular band, one of said fastener parts comprises a plug-in tongue formed with teeth, and the other of said fastener parts comprises a keeper having a passage for receiving said tongue, shoulders for interengaging with said teeth, and a longitudinal groove for slidably receiving an orthodontic appliance, said keeper is provided with a clamping device for securing said keeper to said dental appliance in a selected position, said clamping device comprises a plurality of radial clamping arms which differ in thickness and are angularly spaced apart, and each of said arms is selectively angularly movable to a position in which it protrudes over said groove for slidable and clamping engagement with said orthodontic appliance.

3. A dental fixing element as set forth in claim 2, in which said teeth are side teeth, and said tongue is formed with a central slot and permits of a resilient interengagement between said teeth and shoulders.

4. A dental fixing element as set forth in claim 3, in which said strip metal element is provided with a handle adjacent to said tongue.

5. A dental fixing element as set forth in claim 2, in which said keeper is formed on both sides with longitudinal grooves for receiving tying means for securing said dental appliance to said keeper.

6. A dental fixing element as set forth in claim 2, in which said strip metal element has portions of reduced thickness which are arranged to contact a tooth on its mesial and distal sides when said annular band is fitted around said tooth.

7. A dental fixing element as set forth in claim 6, in which said strip metal element is formed so that said annular band flares toward one side edge of said strip metal element.

8. A dental fixing element as set forth in claim 2, in which said clamping device comprises a rotatable plate which has portions differing in thickness and protruding over said groove.

9. A dental fixing element which is adapted to be fitted as an annular band around a tooth and to be secured to an orthodontic appliance to hold the same in position, comprising a strip metal element having two end portions, which are adapted to overlap in said annular band, two slide-snap fastener parts which are respectively carried by said end portions and selectively interengageable in a plurality of positions which determine respective diameters of said annular band, and a bracket which is carried by said strip metal element and has a longitudinal groove for slidably receiving an orthodontic appliance, said bracket carrying a clamping device which comprises a plurality of radial clamping arms which differ in thickness and are angularly spaced apart, and projects over said groove and is selectively angularly movable to positions for slidable and clamping engagement, respectively, with an orthodontic appliance received in said groove so that the clamping device is adapted to secure said bracket to said orthodontic appliance in a selected position.

10. A dental fixing element which is adapted to be fitted as an annular band around a tooth and to be secured to an orthodontic appliance to hold the same in position, comprising a strip metal element adapted to form said annular band and a bracket which is carried by said strip metal element and has a longitudinal groove for slidably receiving an orthodontic appliance, said bracket carrying a clamping device which comprises a plurality of radial clamping arms which differ in thickness and are angularly spaced apart, and projects over said groove and is selectively angularly movable to positions for slidable and clamping engagement, respectively, with an orthodontic appliance received in said groove so that the clamping device is adapted to secure said bracket to said orthodontic appliance in a selected position.

* * * * *